US009655545B2

(12) United States Patent
Ji et al.

(10) Patent No.: US 9,655,545 B2
(45) Date of Patent: May 23, 2017

(54) APPARATUS FOR MEASURING IN-VIVO MECHANICAL PROPERTIES OF BIOLOGICAL TISSUES

(71) Applicant: The Trustees of Dartmouth College, Hanover, NH (US)

(72) Inventors: Songbai Ji, Lebanon, NH (US); David W. Roberts, Lyme, NH (US); Keith D. Paulsen, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 225 days.

(21) Appl. No.: 14/345,029

(22) PCT Filed: Sep. 17, 2012

(86) PCT No.: PCT/US2012/055755
§ 371 (c)(1),
(2) Date: Mar. 14, 2014

(87) PCT Pub. No.: WO2013/040555
PCT Pub. Date: Mar. 21, 2013

(65) Prior Publication Data
US 2014/0371600 A1    Dec. 18, 2014

Related U.S. Application Data

(60) Provisional application No. 61/535,201, filed on Sep. 15, 2011.

(51) Int. Cl.
*A61B 5/107* (2006.01)
*A61B 5/00* (2006.01)
(Continued)

(52) U.S. Cl.
CPC .......... *A61B 5/1079* (2013.01); *A61B 5/0053* (2013.01); *A61B 5/0077* (2013.01);
(Continued)

(58) Field of Classification Search
None
See application file for complete search history.

(56) References Cited

U.S. PATENT DOCUMENTS

| 5,810,731 A | 9/1998 | Sarvazyan et al. |
| 2002/0080481 A1 | 6/2002 | Tachihara et al. |

(Continued)

FOREIGN PATENT DOCUMENTS

WO    2013109966 A1    7/2013

OTHER PUBLICATIONS

International Search Report and Written Opinion issued in related PCT Patent Application Serial No. PCT/US2015-033672; dated Aug. 19, 2015, 10 pages.

(Continued)

*Primary Examiner* — Jennifer Dieterle
*Assistant Examiner* — Kevin Pontius
(74) *Attorney, Agent, or Firm* — Lathrop & Gage LLP (57) ABSTRACT

An apparatus and method for measuring mechanical properties of tissue has a stereo optical surgical microscope with at least one objective lens and at least two digital cameras such that paired images obtained from the digital cameras form stereo pairs, and a digital image processing system adapted to determine surface topography of tissue from the stereo pairs of images and a resulting surface displacement map as a result from indentation. The apparatus has an one indenter; and mechanical modeling routines stored in memory of the image processing system, the mechanical modeling routines capable of constructing computer models of mechanical properties of tissue, and fitting parameters of the computer model to observed surface displacement maps generated by coregistering surface topography of tissue with and without the indenter positioned on the tissue. In an embodiment, fitted parameters of the computer model are (Continued)

displayed and used to adjust a surgical plan. An apparatus and method for measuring mechanical properties of tissue has a stereo optical surgical microscope with at least one objective lens and at least two digital cameras such that paired images obtained from the digital cameras form stereo pairs, and a digital image processing system adapted to determine surface topography of tissue from the stereo pairs of images and a resulting surface displacement map as a result from indentation. The apparatus has an one indenter; and mechanical modeling routines stored in memory of the image processing system, the mechanical modeling routines capable of constructing computer models of mechanical properties of tissue, and fitting parameters of the computer model to observed surface displacement maps generated by coregistering surface topography of tissue with and without the indenter positioned on the tissue. In an embodiment, fitted parameters of the computer model are displayed and used to adjust a surgical plan.

15 Claims, 3 Drawing Sheets

(51) Int. Cl.
| | | |
|---|---|---|
| *G02B 21/00* | (2006.01) | |
| *G02B 21/36* | (2006.01) | |
| *A61B 90/20* | (2016.01) | |
| *G06T 7/33* | (2017.01) | |
| *A61B 19/00* | (2006.01) | |
| *G06T 7/00* | (2006.01) | |
| *A61B 90/00* | (2016.01) | |

(52) U.S. Cl.
CPC .......... *A61B 90/20* (2016.02); *G02B 21/0012* (2013.01); *G02B 21/367* (2013.01); *G06T 7/344* (2017.01); *A61B 2090/364* (2016.02); *A61B 2090/371* (2016.02); *G06T 2200/04* (2013.01); *G06T 2207/10012* (2013.01); *G06T 2207/10056* (2013.01); *G06T 2207/30016* (2013.01)

(56) References Cited

U.S. PATENT DOCUMENTS

| | | | |
|---|---|---|---|
| 2007/0236514 A1* | 10/2007 | Agusanto | A61B 1/00193 |
| | | | 345/646 |
| 2009/0076732 A1 | 3/2009 | Sprigle et al. | |
| 2009/0180178 A1 | 7/2009 | Luecke et al. | |
| 2011/0054355 A1* | 3/2011 | Hunter | A61B 5/0053 |
| | | | 600/587 |
| 2014/0020476 A1* | 1/2014 | Inoue | G01N 3/08 |
| | | | 73/790 |

OTHER PUBLICATIONS

Najib, et al. "Trancranial Brain Stimulation: Clinical Applications for Future Directions," Neurosurg Clin. N. Am, Retrieved from the Internet: URL: http://www.ncbi.nlm.nih.gov/pmc/articles/PMC3547606/pdf/nihms263566.pdf, Apr. 2011.

Vigneron, et al., "2D XFEM-Based Modeling of Retraction and Successive Resections for Preoperative Image Update.," Comput Aided Surg., Retrieved from Internet: URL: http://www.ncbi.nim.nih.gov/pcm/articles/PMC3843511/pdf/nihms--524531.pdf, 2009.

International Search Report and Written Opinion issued in related PCT Patent Application Serial No. PCT/US2012/055755; dated Feb. 28, 2013, 7 pp.

Miller, Karol, et al., "Mechanical Properties of Brain Tissue In-Vivo: Experiment and Computer Simulation", Journal of Biomechanics 33 (2000) 1369-1376.

* cited by examiner

APPARATUS FOR MEASURING IN-VIVO MECHANICAL PROPERTIES OF BIOLOGICAL TISSUES

RELATED APPLICATIONS

This application is the U.S. national stage of international application PCT/US2012/055755, filed Sep. 17, 2012, which claims priority to U.S. Provisional Application 61/535,201 filed 14 Sep. 2011, the disclosures of which are incorporated herein by reference.

GOVERNMENT INTEREST

The work herein is supported by the National Institutes of Health (NIH) and National Institute of Neurological Disorders and Stroke (NINDS) grant number 1R21 NS078607. The Government has certain rights in this invention.

BACKGROUND

Much interest has developed in mechanical properties of brain tissue because these properties are believed to play a critical role in studying head injuries or simulations of brain deformation during surgery. It is desirable to know these properties so that not only can head injuries be simulated in computer and mechanical models, but that the effect of ameliorative devices, such as helmets, can be tested on computer and mechanical models rather than on live people. For example, when an object strikes a human head, there are effects on the brain both on the "coup" side, where the object struck, and on the opposite or "contra-coup" side; even if the skull remains intact and the brain is not penetrated, these effects can lead to bruising, swelling, confusion, even bleeding and, in some cases, death. The effects on both coup and contra-coup side of the head depend significantly on the dimensions, mechanical and physical properties of brain tissue and surrounding structures, including the skull, meninges, and cerebrospinal fluid, and how the brain is accelerated by the blow, and decelerated by the opposite side of the skull. Among the mechanical properties of brain on which such effects depend are tissue shear stiffness, including time decay constants between short term stiffness for rapid motions, and long term stiffness for slower motions, bulk modulus, density, and viscoelasticity.

Mechanical properties of brain tissue derived from cadavers may be inaccurate due to rapid degenerative changes that begin at death. Material properties of the brain are still poorly understood and existing material models have the instantaneous shear stiffness differing up to two orders in magnitude. This is largely due to the paucity of in vivo brain biomechanical data and variations in mechanical testing schemes and tissue postmortem conditions. Brain tissue is particularly sensitive to anoxia, hours-old tissue is suspected to respond significantly differently than fresh, living, tissue. It is therefore desirable to measure these properties in-vivo.

Arash A. Sabet, Eftychios Christoforouc, Benjamin Zatlin, Guy M. Genin, Philip V. Bayly, *Deformation of the human brain induced by mild angular head acceleration*, Journal of Biomechanics 41 (2008) 307-31, available online at www.JBiomech.com, and Y Feng, T. M. Abney, R. J. Okamoto, R. B. Ness, G. M. Genin and P. V. Bayly *Relative brain displacement and deformation during constrained mild frontal head impact* J. R. Soc. Interface, doi:10.1098/rsif.2010.0210, published online at rsif.royalsocietypublishing.org, describe efforts to use high speed tagged MRI images to measure deformation of the brain under mild acceleration. These high speed tagged MRI images are compared with computer simulations of brain deformation under similar acceleration to validate parameters of those models.

Many people undergo brain surgery each year, often for tumors. Tumors often have mechanical properties significantly different from those of surrounding normal tissue. Measurements of mechanical properties of brain at particular areas near diseased tissue may provide clues to hidden metastases a surgeon may wish to treat.

As part of the surgical process, a craniotomy is generally performed to expose tissue. Once opened, pressure changes due to the craniotomy causes a deformation of brain tissue. The surface of tissue deformed from craniotomy has been mapped with a stereo camera. Models of pre-craniotomy brain shape can be derived from the MRI and CT images available for many patients, and correlated to post-craniotomy brain shape.

The surface of the brain has many convolutions and small blood vessels. Brain surface topography has been mapped by 3-dimensional topography extraction software.

SUMMARY

An apparatus for measuring mechanical properties of tissue has a stereo optical surgical microscope having at least one objective lens, an illuminator, and at least two digital cameras such that paired images obtained from the digital cameras form a stereo pair, and a digital image processing system is configured to determine surface topography of tissue from the stereo pairs of images. The apparatus also has at least one indenter; and mechanical modeling routines stored in memory of the digital image processing system, the mechanical modeling routines capable of constructing a computer model of mechanical properties of tissue, and fitting parameters of the computer model to observed surface topography of tissue without indenter and tissue with the indenter positioned on the tissue.

A method of measuring mechanical properties of tissue includes obtaining a first stereo pair of images of a surface of the tissue; placing an indenter on the tissue; obtaining a second stereo pair of images of the surface of the tissue with the indenter on the tissue; determining a first three-dimensional surface map of the tissue from the first stereo pair; determining a second three-dimensional surface map of the tissue from the second stereo pair; and constructing a computer model of mechanical deformation of the tissue, the model having parameters for at least one parameter selected from the group consisting of tissue shear stiffness, tissue bulk modulus, tissue density, and tissue viscoelasticity; and fitting the parameters of the computer model to the first and second three-dimensional surface maps.

DETAILED DESCRIPTION OF THE EMBODIMENTS

Figure 1:
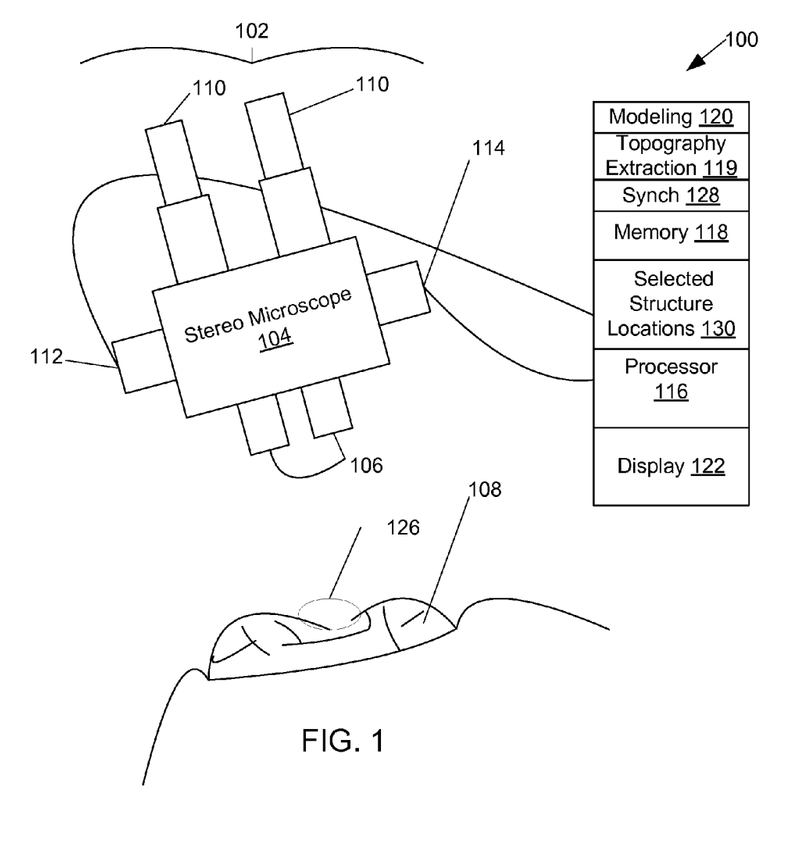
FIG. 1 illustrates an apparatus for measuring deformation of tissue under pressure from an indenter.

An optical deformation-measurement system 100 has a microscopy subsystem 102 with a stereo surgical microscope 104. Stereo surgical microscope 104 is equipped with illumination devices (not shown) as known in surgical microscopes, and has a long reach such that surgical implements (not shown) can be inserted between the microscope's 104 objective lenses 106 and tissue 108 in a focal plane of microscope 104, such as brain tissue, to permit a surgeon to perform surgery under microscopic observation. Microscope 104 is mounted on an adjustable arm (not shown) as known in the art.

The body of stereo surgical microscope 104 has beamsplitters as known in the art of surgical microscopes, such that some light from each objective 106 reaches one of surgeon's eyepieces 110 and a left 112 or right 114 high-resolution digital cameras. Left 112 digital camera is arranged to receive light received from a left portion of the microscope's objective if the microscope has a single objective lens, or from a left objective lens 106 if two objectives are provided, thereby imaging the tissue as viewed from the left. Right 112 digital camera is arranged to receive light received from a right portion of the microscope's objective lens if the microscope has a single lens, or from a right objective lens 106 if two objectives are provided, thereby imaging the tissue as viewed from the right. A pair of simultaneous images, one taken by left camera 112 and one by right camera 114, together form a stereo pair of images.

Digital cameras 112, 114 are coupled to a digital image processor 116 which has memory 118 for storing images, three-dimensional surface-topography extraction routines 119, and modeling routines 120. Processor 116 is also coupled to a display 122 for reporting extracted mechanical properties and measured surface topography.

The processor, microscope, and three-dimensional surface-topography extraction routines are calibrated using at least one 3-d extraction phantom such that the processor is capable of extracting accurate three-dimensional surface topography of brain surface from stereo pairs of images of the brain surface.

The surface of the brain has many features, including convolutions, each providing a small fissure, and also has many small blood vessels. Surface topography extraction routines 119 determines locations of these vessels and fissures in a stereo pair of images, correlates these features found in the two images of the stereo pair to identify the same, or identical, features in each image of the stereo pair, and then compares locations of these features in the stereo images to determine surface topography of the brain tissue. Other tissues and organs may also have nonuniformities of surface; their surface topography may be similarly mapped based on distinctive features on surface.

Indenters 126 are prepared by fabricating smooth disks of predetermined weight and diameter, in an embodiment the indenter is approximately one centimeter in diameter; in an alternative embodiment, such as may be more appropriate with other dimensions of craniotomy, with another size appropriate for the craniotomy dimensions. In a particular embodiment, indenters of twenty-five, fifty, and seventy-five grams mass are prepared; in other embodiments, indenters of other masses are used. Each indenter has a matte surface to avoid generating reflections that may confuse the surface topography extraction routines, and is plated in gold or other material (e.g., Parylene) for biocompatibility. In an embodiment, the indenters are made of gold-plated tungsten, and are autoclaved before each use to ensure sterility. In an alternative embodiment, an upper surface of each indenter is marked with an optically-visible grid pattern such that its surface may be precisely located by surface topography extraction routines such that the measurement system can identify precisely a location of a top surface of the indenter, and then determine from the location of the indenter's top surface and known indenter dimensions a location of a bottom surface of the indenter, and infers from the location of the bottom surface of the indenter a surface topography of a portion of brain hidden by the indenter in the stereo image pair.

When a patient is scheduled for medically-necessary surgery requiring craniotomy as part of that surgery, that patient is asked to give informed consent 202 (FIG. 2) to having mechanical properties of his brain measured and mapped. The patient is then sedated and anesthetized, and positioned 203 such that craniotomy will result in exposed brain being on an upper surface. A craniotomy is then performed 204 and the dura and meninges opened to expose brain tissue surface. Next, the microscope 104 is positioned and surface topology of the exposed brain tissue is mapped 206 by making stereo image pairs with cameras 112, 114 and processing the image pairs in processor 116 using topology extraction routine 119. In order to provide constraints for modeling of physical parameters, craniotomy edges are extracted 207 from the stereo image pairs.

Figure 2:
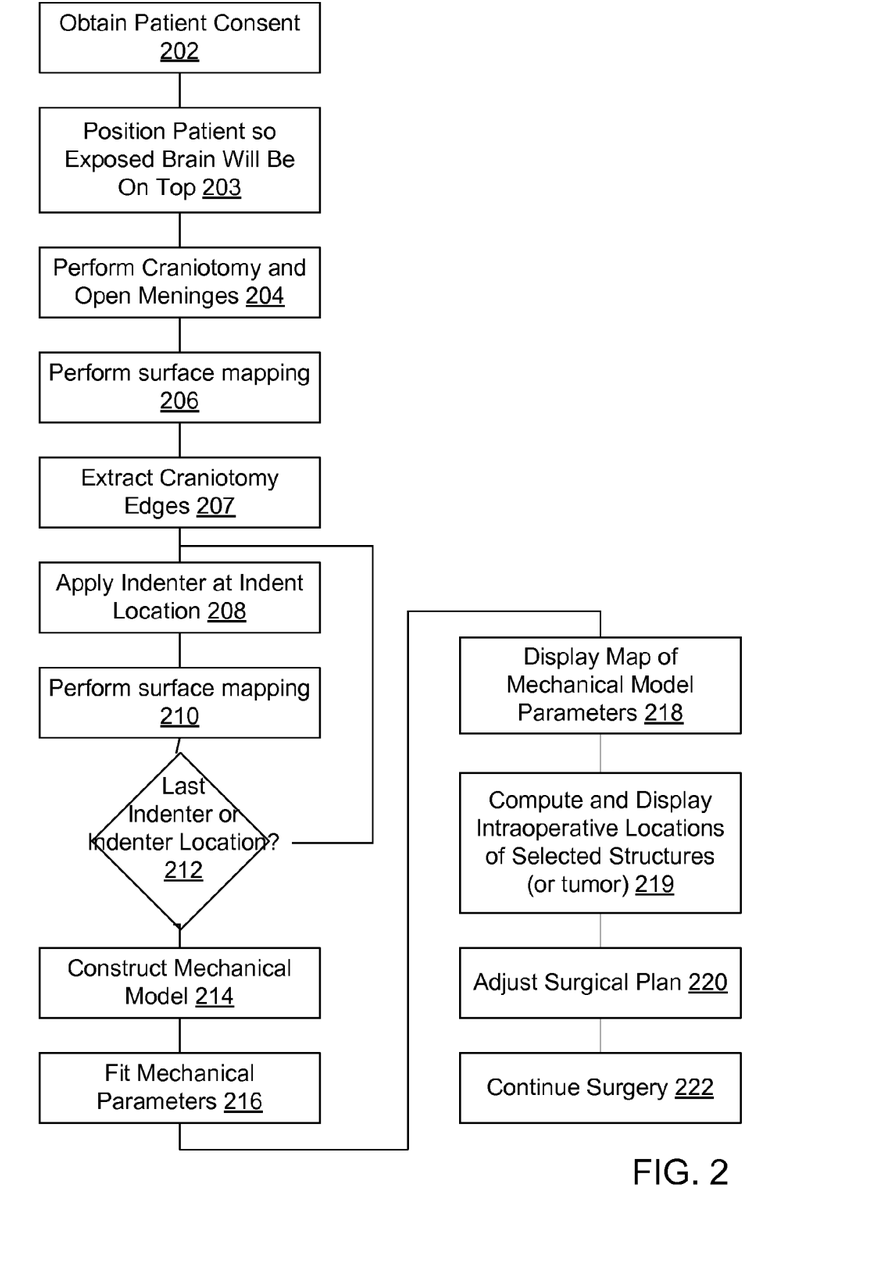
FIG. 2 is a flowchart illustrating a method for extracting mechanical properties of brain tissue.

A selected indenter of the prepared indenters is placed 208 at a predetermined location on exposed tissue 108 within the craniotomy. Three dimensional surface mapping 210 for brain tissue is again performed in processor 116 using topology extraction routine 119 on at least one additional stereo image pair made with cameras 112, 114. The indenter location is identified from the optically-visible pattern marked on the indenter, and an assumed surface of the brain tissue for portions hidden by the indenter is determined from known thickness of the indenter. In an embodiment, the assumed surface of the brain is determined by subtracting a model of the indenter from a model of the surface as determined from stereo image pairs. The indenter is then removed.

A complete surface displacement map is generated by co-registering the surface maps obtained with and without the indenter, and is stored in memory 118 of processor 116.

In an embodiment, additional indenters of the prepared indenters are placed 208 at the same or at other predetermined locations on exposed tissue 108 within the craniotomy; one, two, or three indenters of increasing weight of 25, 50, and 75 grams are placed sequentially with three-dimensional surface mapping performed in processor 116 using topology extraction routine 119 on at least one additional stereo image pair made with cameras 112, 114 after placing each successive indenter, with sequential indenter placement ceasing after an indenter is placed that produces sufficient deformation in the exposed tissue to model physical parameters. In this way an appropriate weight for indenters is determined that produces sufficient deformation for determining mechanical properties of the tissue while keeping indenter weight, and thus load on the tissue, low enough to avoid tissue damage.

In some embodiments, a single indenter is used at a single indenter location.

In an alternative embodiment, a single indenter of predetermined weight is placed on the exposed tissue at locations denoted by a two-by-two or a three-by-three grid within the craniotomy. After each placement, the three dimensional surface mapping 210 is repeated. Repeating continues until 212 the last indenter is placed in the last predetermined location. All surface maps generated with indenters 210 and without indenters 206 are retained.

In an alternative embodiment, stereo pairs of images from cameras 112, 114 are stored in memory 118, and three dimensional surface mapping 210 is performed after stereo pairs have been captured with all indenters in all indenter locations used with a particular patient.

Figure 3:
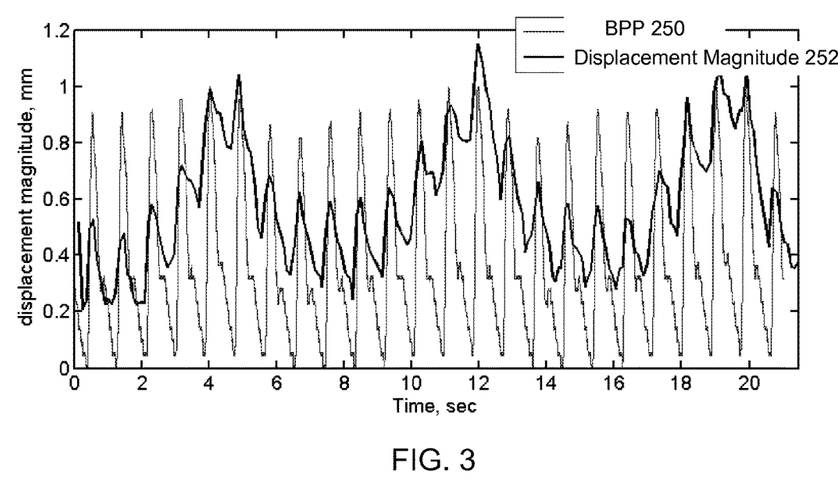
FIG. 3 is an illustration of displacement of brain surface features with instantaneous blood pressure.

It has been observed that the surface of some organs as exposed during surgery, including the human brain, moves synchronously with blood pressure pulsations (BPP, 250), and with respirations. Blood pressure pulsations are surface deformations as blood pressure changes throughout the cardiac cycle. A magnitude of displacement 252 synchronous to BPP 250 is illustrated in FIG. 3.

In an embodiment, image acquisition for surface mapping is timed by synchronization routines 128 to occur at a same blood pressure point in the cardiac pulse cycle, as determined from an electrocardiographic monitor or pulse oximeter, of the patient in order to compensate for blood pressure pulsations.

In an alternative embodiment a sequence of stereo image pairs are acquired by topography extraction routines 119 for a predetermined time interval, with surface mapping performed for each image pair, and an average surface shape determined through the interval to compensate for blood pressure pulsations. In a particular embodiment, average surface shape is determined across 5 respiration cycles or approximately 50 harmonic heartbeats to characterize brain surface profile both before and after applying the indenter to the brain tissue surface. In embodiments, respiration cycles and heartbeats are determined by an electrocardiographic monitor, and in other embodiments by pulse oximetry.

In an embodiment, surface mapping is refined across multiple respiration cycles or heartbeats by topography extraction routines 119 by computing cortical surface deformation of indenter-absent and indenter-present image sequences relative to a first image of each sequence with optical flow motion tracking; using fast Fourier transforms to detect the fundamental frequencies in motion corresponding to patient respiration and BPP; obtaining images across a multiple of harmonic cycles and a corresponding number of image frames for averaging cortical surface motion; and computing an average cortical surface profile.

A computer model of the mechanical properties of the brain is constructed 214; in an embodiment the model uses a hexahedral mesh model with separate model parameters for each region of the model, each region typically containing multiple elements of the mesh model, where each element represents a small volume of the tissue. Model parameters include the initial shear modulus ($\mu 0$), incompressibility or bulk modulus (K0), and terms related to viscoelasticity at each element of the mesh. The outer surface of the brain mesh is first deformed to match with the surface obtained without indenter in place by projecting the surface nodes on to that obtained from stereovision. The resulting brain mesh will serve as the undeformed reference for subsequent model simulation. The model is then constrained by the craniotomy opening, and has applied force and position terms that model the applied indenters on surface elements of the computer model at the applied indenter location. The model is constructed, and deformation under the applied force modeled, by modeling routines 120.

In an embodiment, the model is constructed using, and constrained, by extracting tissue types and boundaries from a pre-operative magnetic resonance image (MRI) in three dimensions. Deformation of the brain mesh due to indentation is modeled, and the mesh model is constrained such that similar tissue types have similar parameters. In a particular embodiment, the model provides separate shear modulus, bulk modulus, and viscoelastic terms for brainstem, cerebellar, and cerebral tissue types.

In other embodiments, including embodiments where multiple indenter locations are used to provide sufficient data for high resolution, regional boundaries of the model are constrained from pre-operative magnetic resonance imaging to follow boundaries of identifiable tissue types and boundaries structures identifiable in preoperative MRI such as brainstem, cerebellum, cerebrum, and tumor; further, each region having separately fit parameters is considerably smaller than those structures. In a particular embodiment, a smaller region size is used for regions near tumor than for other regions within the same identifiable structure to permit recognition of regions that may contain invasive tumor extensions.

Material parameters of the mesh computer model, including parameters for tissue shear stiffness, bulk modulus, density, and viscoelasticity, are then fit 216 to the displacement map generated by comparing and registering the with and without indenter tissue-surface maps stored in memory 118.

In an alternative embodiment, in order to more rapidly converge on fitted parameters for small regions, these parameters are constrained to be equal across large regions of the model in an initial pass of fitting. Once these parameters are determined for the large regions, these constraints are removed and the parameters are constrained to be equal across smaller regions of the model for a second, or refining, round of fitting using parameters from the first, or coarse, pass as initial guesses. In an embodiment, the refining round of fitting uses a simulated-annealing fit algorithm.

Fitted parameters of the three dimensional mechanical model are then output on display 122. In an embodiment, fitted parameters of the model are displayed 218 as a map of selected fitted parameters at predetermined depths in tissue, and are effectively displayed as tomographic mechanical-property maps.

It is expected that some tumor types will have mechanical properties that will vary from properties of normal tissue, and that the tomographic mechanical property maps may be of use in locating tumor extensions. It is also expected that tumors of different types will have differing mechanical properties; this may provide useful information to supplement pathology reports derived from examination of removed tissue.

Once the fitted mechanical parameters are displayed, in some cases a surgeon may use the displayed maps of selected parameters to modify 220 a surgical plan to more completely remove tumor. Surgery is then continued 222, following an original or a modified surgical plan as the surgeon deems appropriate, which typically includes closing the meninges and craniotomy.

While MRI, CT, and similar imaging technologies are often used to define tumors before surgery, these images are often key to developing a surgical plan. The brain, however, is soft enough to deform somewhat during craniotomy, and may deform further during surgery as pressure is applied by surgeons and their assistants. This deformation causes tumor and its extensions, or other pathological tissue, to shift relative to bony landmarks.

In an embodiment, the mechanical properties of the brain, such as the fit parameters derived from the afore-described measurement, are also useful as parameters for a computer modeling of the brain that can be used to show a surgeon mid-operation intraoperative locations 219 of pathological tissue—showing where the pathological tissue has moved because of these deformations. Similarly, robotic surgical devices can also be corrected for such intraoperative induced shifts in tissues. Further, they can also show intraoperative locations of important structures within the brain that a surgeon intends to preserve.

In an embodiment, a surface map of the tissue, such as a brain, is determined prior to craniotomy by analysis of pre-operative MRI and CT images that show preoperative locations 219 of some of the same fissures and surface blood vessels that are imaged in the post-craniotomy stereo pairs. Locations of particular selected structures, including locations of any tumor present in the preoperative MRI and CT images, are marked in the mesh computer model. After parameters of the mesh computer model have been fit and displayed, the three dimensional mesh computer model, already constrained for the craniotomy, is constrained to an initial state having a surface map determined from the MRI and CT images, and preoperative locations 130 of the particular selected structures are annotated onto the model. The model is adjusted to model applied pressures and presence of foreign objects such as surgical tools and retractors during surgery, and the model is constrained to deform to a surface map determined from intraoperative stereo images. The model is then re-run to compute or determine intraoperative induced locations of the particular selected structures. These computed locations are then displayed 219 to a surgeon, who then uses the displayed intraoperative induced locations to locate the selected structures, and adapt his surgical plan 220 to remove or preserve them as appropriate.

While the foregoing discussion has focused on brain tissues, other soft tissues are also subject to induced shifts during surgery. The herein-described procedure of exposing tissue, of determining pre-indenter surface contours with a stereo surgical microscope and an image processing system, applying calibrated indenters, determining post-indenter surface contours, computer modeling and fitting parameters of the computer model to the measured surface contours, is applicable to determining mechanical properties of other tissues; using the fit parameters in the model may prove useful in modeling intra-operative locations of lesions in liver.

Various combinations of features herein described may be present in any one embodiment. A partial list is as follows:

In an embodiment designated A, an apparatus for measuring mechanical properties of tissue has a stereo optical surgical microscope with at least one objective lens, an illuminator, and at least two digital cameras, such that a first camera is coupled to provide digital images of the tissue as observed from the left, and a second camera is coupled to provide digital images of the tissue as observed from the right through the at least one objective lens, paired images obtained from the first and second camera forming a stereo pair; a digital image processing system adapted to determine surface topography of tissue from stereo pairs of images obtained by the at least two digital cameras; at least one indenter; and mechanical modeling routines stored in memory of the digital image processing system adapted to constructing a computer model of mechanical properties of tissue, and fitting parameters of the computer model to observed surface topography of tissue without indenter on the tissue and surface topography of the tissue with the indenter positioned on the tissue.

In an embodiment designated AA, the apparatus designated A further comprising a display system for displaying a map of fitted parameters of the computer model.

In an embodiment designated AB, the apparatus designated A wherein the memory is further configured to store preoperative locations of particular selected structures, and wherein the mechanical modeling routines are further adapted to determine intraoperative locations of the particular selected structures using the fitted parameters.

In an embodiment designated AC, the apparatus designated A, AA, or AB wherein the image processing system is adapted to determine the surface topography of the tissue by subtracting a model of the indenter from surface topography determined from stereo pairs of images.

In an embodiment designated AD, the apparatus designated A, AA, or AB wherein the image processing system is configured to compensate for blood pressure pulsations in determining a surface topography from stereo image pairs.

In an embodiment designated AE, the apparatus designated AD wherein the compensation for blood pressure pulsations is performed by synchronizing image capture to a heartbeat as determined by an electrocardiographic monitor or pulse oximeter.

In an embodiment designated AF, the apparatus designated AD wherein the compensation for blood pressure pulsations is performed by averaging surface profile across at least one cardiac cycle as determined by an electrocardiographic monitor or pulse oximeter.

In an embodiment designated B, a method of measuring mechanical properties of tissue includes obtaining a first stereo pair of images of a surface of the tissue; placing an indenter on the tissue; obtaining a second stereo pair of images of the surface of the tissue with the indenter on the tissue; determining a first three-dimensional surface map of the tissue from the first stereo pair; determining a second three-dimensional surface map of the tissue from the second stereo pair; determining the resulting displacement map as a result of the indentation; constructing a computer model of mechanical deformation of the tissue, the model having parameters for at least one parameter selected from the group consisting of tissue shear stiffness, tissue bulk modulus, tissue density, and tissue viscoelasticity; and fitting the parameters of the computer model to produce the displacement map generated form the first and second three-dimensional surface maps.

In an embodiment designated BA, the method designated B wherein the computer model of mechanical deformation of the tissue is a mesh model having a plurality of elements, the elements being grouped into multiple regions, and wherein the parameters are fit separately for each region of the mesh model.

In an embodiment designated BB, the method designated B wherein the tissue is brain tissue, and further comprising extracting a craniotomy boundary from the first stereo image pair, and constraining the computer model with the craniotomy boundary.

In an embodiment designated BC, the method designated BB further comprising displaying the determined fitted parameters, comparing the determined parameters to standard values, and modifying a surgical plan based upon the displayed parameters.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An apparatus for measuring mechanical properties of tissue comprising:
   a stereo optical surgical microscope comprising:
      at least one objective lens,
      an illuminator, and
      at least a first and a second digital cameras, such that a first digital camera is coupled to provide digital images of the tissue as observed from a first angle, and a second digital camera is coupled to provide digital images of the tissue as observed from a second angle-through the at least one objective lens, paired images obtained from the first and second camera forming a stereo pair;
   a digital image processing system adapted to determine surface topography of tissue from stereo pairs of images obtained by the at least two digital cameras;
   at least one indenter; and
   mechanical modeling routines stored in memory of the digital image processing system, the mechanical modeling routines adapted to construct a computer model of mechanical properties of tissue, and fitting parameters of the computer model to a measured displacement map obtained by co-registering surface topography of tissue without indenter on the tissue and surface topography of the tissue with the indenter positioned on the tissue;
   the apparatus further comprising a display system for displaying a map of fitted parameters of the computer model;
   wherein the memory is further configured to store preoperative locations of particular selected structures, and wherein the mechanical modeling routines are further adapted to determine intraoperative locations of the particular selected structures using the fitted parameters;
   wherein the image processing system is configured to determine the surface topography of the tissue by subtracting a model of the indenter from surface topography determined from stereo pairs of images.

2. The apparatus of claim 1, wherein the image processing system is configured to compensate for blood pressure pulsations in determining a surface topography from stereo image pairs.

3. The apparatus of claim 2 wherein the compensation for blood pressure pulsations is performed by synchronizing image capture to a heartbeat as determined by an electrocardiographic monitor or pulse oximeter.

4. The apparatus of claim 2 wherein the compensation for blood pressure pulsations is performed by averaging surface profile across at least one cardiac cycle as determined by an electrocardiographic monitor or pulse oximeter.

5. A method of measuring mechanical properties of tissue comprising:
   obtaining a first stereo pair of images of a surface of the tissue;
   placing an indenter on the tissue;
   obtaining a second stereo pair of images of the surface of the tissue with the indenter on the tissue;
   determining a first three-dimensional surface map of the tissue from the first stereo pair;
   determining a second three-dimensional surface map of the tissue from the second stereo pair;
   determining the resulting surface displacement map as a result from indentation by coregistering the first and second three-dimensional surface maps;
   constructing a computer model of mechanical deformation of the tissue, the model having parameters for at least one parameter selected from the group consisting of tissue shear stiffness, tissue bulk modulus, tissue density, and tissue viscoelasticity; and
   fitting the parameters of the computer model to the three-dimensional surface displacement map.

6. The method of claim 5 wherein the computer model of mechanical deformation of the tissue is a mesh model having a plurality of elements, the elements being grouped into multiple regions, and wherein the parameters are fit separately for each region of the mesh model.

7. The method of claim 6 wherein the tissue is brain tissue, and further comprising
   extracting a craniotomy boundary from the first stereo image pair, and
   constraining the computer model with the craniotomy boundary.

8. The method of claim 7 further comprising displaying the fitted parameters, comparing the determined parameters to standard values, and modifying a surgical plan based upon the displayed parameters.

9. A method for measuring mechanical properties of tissue comprising:
   surgically exposing an organ having a lesion;
   using a stereo optical system to obtain at least one pre-indentation stereo pair of images of the organ, and using a digital image processing system to determine a pre-indentation surface topography of the organ from the pre-indentation stereo pair;
   placing at least one indenter on the organ;
   using the stereo optical system to obtain at least one post-indentation stereo pair of images of the organ, and using a digital image processing system to determine a post-indentation surface topography of the organ from the post-indentation stereo pair;
   determining a displacement map by coregistering the pre and post indentation surface topography and determining displacement therebetween;
   fitting parameters of a computer model of mechanical properties of the organ to the measured displacement map to determine mechanical properties of the organ, the computer model being a mesh model having parameters at elements of for at least one parameter selected from the group consisting of tissue shear stiffness, tissue bulk modulus, tissue density, and tissue viscoelasticity;
   using the computer model and preoperative locations of particular selected structures to determine intraoperative locations of the particular selected structures using the fitted parameters.

10. The method of claim 9 wherein the lesion is a tumor, wherein a particular selected structure of the selected structures is the tumor, and further comprising removing at least a portion of the tumor.

11. The method of claim 9 further comprising mapping mechanical properties of the organ.

12. An apparatus for measuring mechanical properties of tissue comprising:
   a stereo optical surgical microscope comprising:
      at least one objective lens,
      an illuminator, and
      at least a first and a second digital cameras, such that a first digital camera is coupled to provide digital images of the tissue as observed from a first angle, and a second digital camera is coupled to provide digital images of the tissue as observed from a second angle-through the at least one objective lens, paired images obtained from the first and second camera forming a stereo pair;

a digital image processing system adapted to determine surface topography of tissue from stereo pairs of images obtained by the at least two digital cameras;

at least one indenter; and mechanical modeling routines stored in memory of the digital image processing system, the mechanical modeling routines adapted to construct a computer model of mechanical properties of tissue, and fitting parameters of the computer model to a measured displacement map obtained by co-registering surface topography of tissue without indenter on the tissue and surface topography of the tissue with the indenter positioned on the tissue;

the apparatus further comprising a display system for displaying a map of fitted parameters of the computer model;

wherein the image processing system is configured to determine the surface topography of the tissue by subtracting a model of the indenter from surface topography determined from stereo pairs of images.

13. The apparatus of claim 12, wherein the image processing system is configured to compensate for blood pressure pulsations in determining a surface topography from stereo image pairs.

14. The apparatus of claim 13 wherein the compensation for blood pressure pulsations is performed by synchronizing image capture to a heartbeat as determined by an electrocardiographic monitor or pulse oximeter.

15. The apparatus of claim 13 wherein the compensation for blood pressure pulsations is performed by averaging surface profile across at least one cardiac cycle as determined by an electrocardiographic monitor or pulse oximeter.

* * * * *

UNITED STATES PATENT AND TRADEMARK OFFICE
CERTIFICATE OF CORRECTION

PATENT NO. : 9,655,545 B2
APPLICATION NO. : 14/345029
DATED : May 23, 2017
INVENTOR(S) : Songbai Ji et al.

Page 1 of 1

It is certified that error appears in the above-identified patent and that said Letters Patent is hereby corrected as shown below:

In the Specification

At Column 1, Lines 15-18:
"The work herein is supported by the National Institutes of Health (NIH) and National Institute of Neurological Disorders and Stroke (NINDS) grant number 1R21 NS078607. The Government has certain rights in this invention."

Should read:
-- This invention was made with government support under grant numbers NS078607, R01 EB002082, and R01 CA159324 awarded by the National Institutes of Health. The government has certain rights in the invention. --

Signed and Sealed this
Fifth Day of November, 2019

Andrei Iancu
*Director of the United States Patent and Trademark Office*